United States Patent [19]

Koh

[11] Patent Number: 4,775,003

[45] Date of Patent: Oct. 4, 1988

[54] LABORATORY MATERIALS AND APPARATUS SUPPORT AND LAMINAR FLOW THERMAL TRANSFER DEVICE

[76] Inventor: John K. Koh, 2593 Esch, Ann Arbor, Mich. 48104

[21] Appl. No.: 30,583

[22] Filed: Mar. 27, 1987

[51] Int. Cl.$^4$ .............................................. F28F 3/00
[52] U.S. Cl. .............................. 165/80.5; 165/104.31; 165/170; 422/104
[58] Field of Search ................... 165/80.5, 80.4, 170, 165/104.31; 126/432

[56] References Cited

U.S. PATENT DOCUMENTS

| | | | |
|---|---|---|---|
| 4,048,981 | 9/1977 | Hobbs | 126/432 |
| 4,527,620 | 7/1985 | Pedersen et al. | 165/80.5 |
| 4,603,466 | 8/1986 | Morley | 165/80.5 |

Primary Examiner—Albert W. Davis, Jr.
Attorney, Agent, or Firm—James M. Deimen

[57] ABSTRACT

A heat transfer device particularly adapted to cool electrophoresis gels and apparatus and comprising a supporting structure and a flat plate spaced above the supporting structure by a peripheral gasket to support the plate. The flat plate, gasket and supporting structure form a shallow enclosed chamber. A pair of longitudinal apertures adjacent opposite ends of the chamber provide communication with a pair of reservoirs in the supporting structure. A pump communicates with the downstream reservoir to draw coolant fluid through the chamber at a rate of flow providing laminar flow in the fluid and drawing the flat plate and gasket tight to the supporting structure.

15 Claims, 1 Drawing Sheet

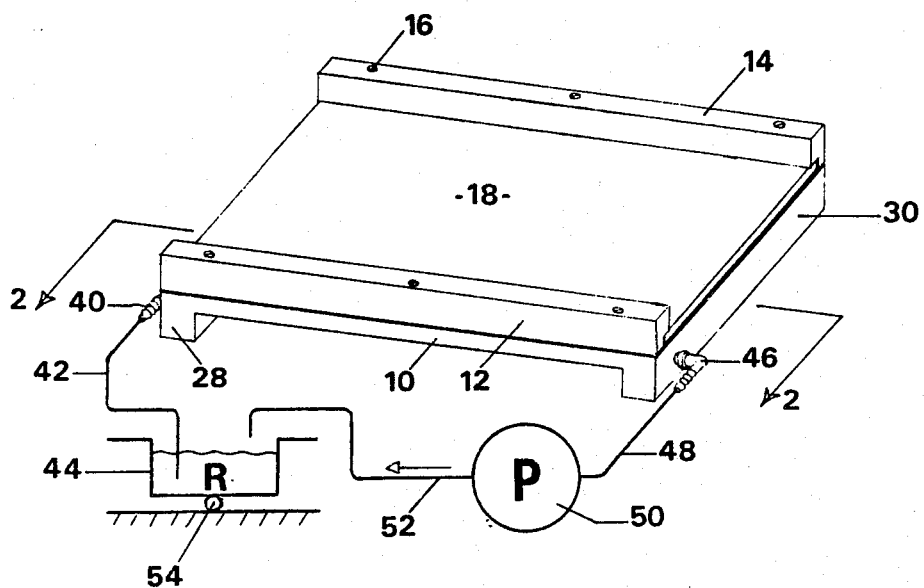
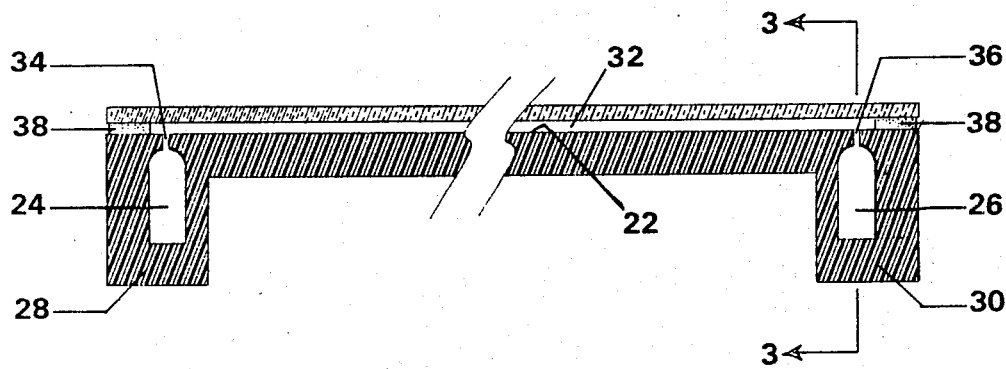
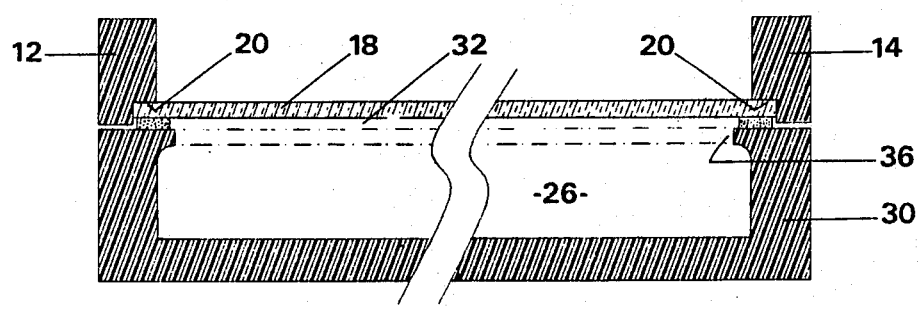
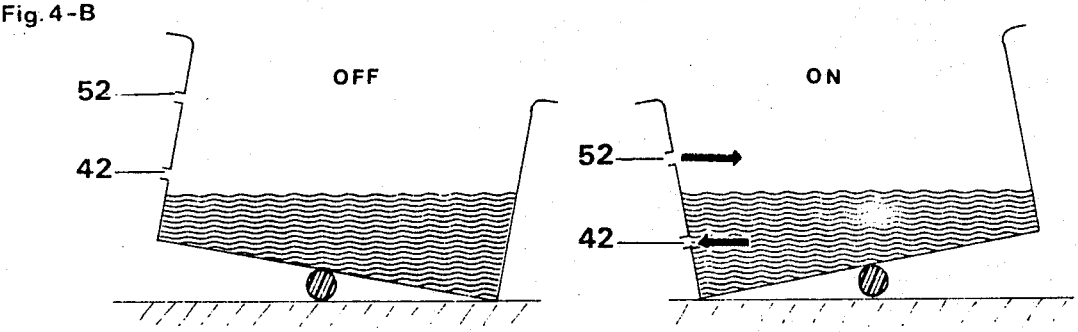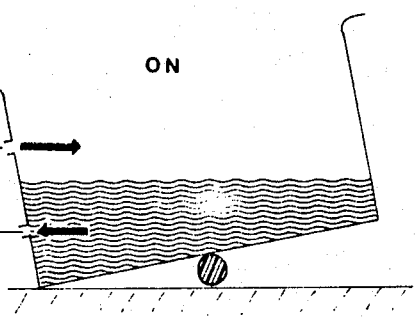

LABORATORY MATERIALS AND APPARATUS SUPPORT AND LAMINAR FLOW THERMAL TRANSFER DEVICE

BACKGROUND OF THE INVENTION

The field of the invention comprises devices to provide thermal transfer to a moving fluid and, in particular, to devices that utilize a moving fluid to heat or cool laboratory materials and apparatus.

Much scientific equipment and material for laboratory use such as electrophoresis gels and apparatus is cooled or heated by placing the gel or apparatus on a glass plate, in turn provided with a supporting structure and means to pass a fluid underneath the glass plate. Typically, the supporting structure includes tubes or grooves through which the fluid passes underneath the plate. The fluid is either heated or cooled to provide the necessary heat transfer from the laboratory materials or apparatus thereabove. The glass plate must be evenly heated or cooled for extended periods of time to prevent hot spots or cool spots which could damage the materials or disturb the operation of the laboratory apparatus and therefore interfere with the results from the operation of the laboratory apparatus.

SUMMARY OF THE INVENTION

The new heat transfer device provides a very shallow chamber beneath the flat plate and means to supply fluid from a reservoir through a longitudinal aperture adjacent one end of the flat plate. A second longitudinal aperture adjacent the opposite end of the flat plate communicates with a second reservoir in the supporting structure which, in turn, is connected to a fluid pump. The pair of longitudinal apertures provide for an even flow of fluid through the shallow chamber. The fluid pump draws the fluid through the chamber under laminar flow conditions, thereby creating in the chamber a negative pressure differential relative to the external environment and thereby drawing the flat plate down tight against the peripheral gasket about the outside of the chamber. Thus, in operation, the gasket, which forms a periphery about the shallow chamber, maintains a tight seal during pump operation but when operation is stopped, the seal is relaxed and the flat plate can be easily removed.

The glass plate should be easily removeable from the supporting structure but nevertheless retain a tight seal with the supporting structure to prevent leakage of the heat transfer fluid flowing in contact with the lower surface of the glass plate. Moreover, leakage of fluid during operation is to be avoided to prevent any possible contamination of the gel or experimental apparatus resting on the glass plate.

DESCRIPTION OF THE DRAWINGS

FIG. 1 is a perspective view of the laminar flow thermal transfer device;

FIG. 2 is a cross section of the device taken along the line 2—2 of FIG. 1;

FIG. 3 is a cross section of the device taken along the line 3—3 in FIG. 2; and

FIGS. 4a and 4b illustrate a rocking reservoir to supply fluid.

DESCRIPTION OF THE PREFERRED EMBODIMENT

Illustrated in FIG. 1, is a supporting structure 10 generally in the shape of an upside down shallow "U". Atop the supporting structure 10 are a pair of side rails 12 and 14, affixed to the structure with long screws 16. Atop the supporting structure 10 and between the side rails 12 and 14, is a glass plate 18, which is nominally held to the supporting structure by notches 20 in the side rails 12 and 14 as best shown in FIG. 3. As shown in FIGS. 2 and 3, the supporting structure 10 has a flat upper surface 22 and reservoirs 24 and 26, which extend substantially across and inside the legs 28 and 30 which, in turn, extend across the ends of the supporting structure 10. The reservoirs 24 and 26 communicate with the chamber 32 beneath the glass plate 18 through longitudinal apertures 34 and 36. Forming the periphery of the chamber 32 is a soft rubber gasket 38, upon which rests the glass plate 18.

Communicating with the inlet reservoir 34 is a small pipe fitting 40, to which may be attached plastic tubing or other suitable piping 42 leading to a supply of fluid such as an external reservoir 44. Reservoir 26 communicates through a similar fitting 46 and piping 48 to a pump 50 from which the fluid is discharged 52. Thus, operation of the pump 50 draws fluid from the external reservoir 44 through the reservoir 24 in the supporting structure 10, through the chamber 32, through the reservoir 26 in the supporting structure 10 and through the discharge at 52.

As best shown in FIG. 3, the aperature 36, as well as the aperture 34 shown in FIG. 2, extend substantially completely across the ends of the chamber 32. In the preferred embodiment, the height of the gasket 38 is substantially 60 mils, thus creating a chamber height of substantially 60 mils. As the fluid is drawn from the external reservoir 44 through the device, the fluid is spread and flows as a sheet that moves progressively beneath and in contact with the undersurface of the glass plate 18. For most purposes, the fluid most suitable is water.

In a typical application for gel electrophoresis, the water is cooled below ambient in the external reservoir 44 and drawn under the plate 18 to cool the plate and the gel thereabove. The 60 mil depth or height of the chamber 32 has been found to be the optimum for laminar flow and best negative pressure differential between the chamber 32 and the ambient over the range of glass plates 18 from three square inches to one and one-half square feet. A suitable minimum flow rate is ¾ gallons per minute, however, for higher flow rates a pump with an adjustable capacity up to 5 gallons per minute is preferred. Thus, the downstream pump 50, in combination with a flow rate providing laminar flow in the chamber, effectively sucks the glass plate 18 down tightly against the gasket 38 and supporting structure 10 to form a tight seal in operation. When the pump 50 is shut off, the glass plate 18 may be easily slid endwise from the side rails and replaced. The screws 16 retaining the side rails to the supporting structure 10 may be loosened if necessary.

The supporting structure may be fabricated from plastic or metal and a metal or ceramic plate substituted for the glass plate. Depending on the coolant requirements necessary, the external reservoir 44 may be filled with water and ice cubes or a refrigerated or heated continuous supply of water provided.

FIGS. 4a and 4b illustrate a rocking external reservoir 44. In FIG. 4a the reservoir supplies fluid to tube 42 and in FIG. 4b the reservoir is tipped about the fulcrum 54 to prevent fluid from entering tube 42. Thus, the fluid flow can be started and stopped almost instantly without shutting off the pump 50.

I claim:

1. A laboratory materials and apparatus support and laminar flow thermal transfer device comprising, a supporting structure having a rectangular flat upper surface, a flat plate for supporting laboratory materials and apparatus, said flat plate spaced above and parallel to the flat upper surface, a peripheral gasket supporting the flat plate above the flat upper surface to form an enclosed chamber therebetween, a pair of longitudinal apertures opening into the chamber adjacent opposite ends thereof and extending substantially across the ends, said apertures each communicating with fluid reservoirs, one being an upstream reservoir and the other being a downstream reservoir, means to nominally retain the flat plate to the gasket and supporting structure, means to supply a substantially incompressible fluid to the upstream reservoir and means to forcefully draw said fluid from the downstream reservoir at a flow rate limited to provide laminar fluid flow substantially throughout the chamber and a static pressure within the chamber less than the pressure outside the flat plate thereby drawing the flat plate tightly to the gasket and supporting structure to prevent leakage of fluid by the gasket.

2. The laboratory materials and apparatus support and laminar flow thermal transfer device of claim 1 wherein the means to forcefully draw the fluid from the downstream reservoir comprises a pump.

3. The laboratory materials and apparatus support and laminar flow thermal transfer device of claim 1 wherein at least one reservoir is located within the supporting structure.

4. The laboratory materials and apparatus support and laminar flow thermal transfer device of claim 1 wherein the distance between the flat upper surface and the flat plate is approximately 60 mils and the fluid is water.

5. The laboratory materials and apparatus support and laminar flow thermal transfer device of claim 1 wherein the distance between the flat upper surface and the flat plate is 60 mils and the flat plate is glass.

6. The laboratory materials and apparatus support and laminar flow thermal transfer device of claim 1 wherein the rectangular area of the flat upper surface is from three square inches to two hundred sixteen square inches in extent.

7. The laboratory materials and apparatus support and laminar flow thermal transfer device of claim 1 wherein the fluid pressure within the entire chamber is less than the atmospheric pressure outside the chamber to thereby draw the flat plate tightly down upon the gasket and supporting structure.

8. A laboratory materials and apparatus support and laminar flow thermal transfer device comprising, a supporting structure having a flat upper surface forming the bottom of a fluid chamber, a plate for supporting laboratory materials and apparatus, said flat plate spaced above the supporting surface and having a flat lower surface forming the top of said fluid chamber, a peripheral gasket supporting the plate on the supporting structure and enclosing the chamber about the chamber periphery, a pair of longitudinal apertures forming inlet and outlet ports to the chamber and located adjacent the chamber periphery at opposite extremes of the chamber, and inlet and outlet reservoirs in communication with the inlet and outlet ports respectively, said plate and supporting structure so spaced as to provide laminar flow in a substantially incompressible fluid drawn through said chamber by means downstream in communication with the outlet reservoir thereby causing the static pressure within the chamber to be less than the atmospheric pressure on the plate and thereby drawing the plate tightly to the gasket and supporting structure to prevent leakage of fluid by the gasket.

9. The laboratory materials and apparatus support and laminar flow thermal transfer device of claim 8 including nominal means to retain the plate to the supporting structure.

10. The laboratory materials and apparatus support and laminar flow thermal transfer device of claim 8 wherein the downstream means comprises a pump drawing fluid from the downstream reservoir.

11. The laboratory materials and apparatus support and laminar flow thermal transfer device of claim 8 wherein at least one reservoir is located within the supporting structure.

12. The laboratory materials and apparatus support and laminar flow thermal transfer device of claim 8 wherein the distance between the bottom and top chamber surfaces is approximately 60 mils.

13. The laboratory materials and apparatus support and laminar flow thermal transfer device of claim 12 wherein the plate is glass and the fluid is water.

14. The laboratory materials and apparatus support and laminar flow thermal transfer device of claim 8 wherein the area of either chamber surface is from three square inches to two hundred sixteen square inches.

15. The laboratory materials and apparatus support and laminar flow thermal transfer device of claim 8 wherein the fluid is cooled below ambient temperature to cool an electrophoresis gel plate.

* * * * *